United States Patent
Cozens

(10) Patent No.: US 6,770,719 B2
(45) Date of Patent: Aug. 3, 2004

(54) METHOD FOR PRODUCING PEROXYDICARBONATES AND THEIR USE IN THE RADICAL POLYMERIZATION OF MONOMERS

(75) Inventor: Ross James Cozens, Strongsville, OH (US)

(73) Assignee: Oxy Vinyls, L.P., Dallas, TX (US)

( * ) Notice: Subject to any disclaimer, the term of this patent is extended or adjusted under 35 U.S.C. 154(b) by 100 days.

(21) Appl. No.: 10/132,582

(22) Filed: Apr. 25, 2002

(65) Prior Publication Data

US 2003/0004366 A1 Jan. 2, 2003

Related U.S. Application Data

(62) Division of application No. 09/433,907, filed on Nov. 4, 1999, now Pat. No. 6,433,208.

(51) Int. Cl.$^7$ .................................................. C08F 4/34
(52) U.S. Cl. .................... 526/230.5; 526/344; 526/932; 526/910; 526/911; 524/800; 524/804; 558/264
(58) Field of Search .............................. 526/230.5, 344, 526/932, 910, 911; 524/800, 804; 558/264

(56) References Cited

U.S. PATENT DOCUMENTS 6,258,906 B1 * 7/2001 Bodart ........................ 526/227

* cited by examiner

Primary Examiner—William Cheung
(74) Attorney, Agent, or Firm—T. Dean Simmons; Richard D. Fuerle

(57) ABSTRACT

A process for producing peroxydicarbonates comprising first reacting at least one inorganic peroxide with at least one alkali metal hydroxide to form at least one alkali metal peroxide. The at least one alkali metal peroxide is added to a mixture of at least one haloformate, at least one dispersant and water. The mixture is homogenized during the entire reaction to form a peroxydicarbonate. The peroxydicarbonate is dispersed as small droplets of from 1 to 10 microns in size in the aqueous mixture. The entire mixture is added to a polymerization reactor containing an ethylenically unsaturated monomer. The peroxydicarbonate functions as the free radical initiator to polymerize the monomer. The peroxydicarbonate is substantially free of organic solvents and plasticizers. The resulting polymers are of high quality.

21 Claims, No Drawings

METHOD FOR PRODUCING PEROXYDICARBONATES AND THEIR USE IN THE RADICAL POLYMERIZATION OF MONOMERS

This application is a division of application Ser. No. 09/433,907, filed Nov. 4, 1999, now U.S. Pat. No. 6,433,208.

BACKGROUND OF THE INVENTION

Peroxydicarbonates are important for use as free radical producing initiators in the polymerization field, and particularly in the polymerization of ethylenically unsaturated monomers, such as vinyl chloride. Peroxydicarbonates are typically made in large batches and sold in pure form either as neat or diluted products. Polymer producers must store large quantities of the peroxydicarbonates for use in their polymerization processes. Precautions must be taken with the storage and handling of these materials as they are unstable and are sensitive to both thermal and impact shock and can detonate under certain conditions. Complying with all of the safety requirements of handling these materials results in the peroxydicarbonates being very expensive to employ in the manufacture of polymers.

Various solutions to this problem have been proposed in the past. U.S. Pat. No. 4,359,427 proposes a process to continuously produce and purify the peroxydicarbonates on the polymerization site and to store them in a diluted phase until used. Another approach that has been suggested is to produce the peroxydicarbonates in the large polymerization vessel before adding the polymerizable monomer. Making the peroxydicarbonates in a large vessel has resulted in quality problems for the polymer being produced for several reasons. One such reason is that there is not adequate mixing of the small amount of reactants in a large reactor vessel. Without adequate mixing the reaction to form the peroxydicarbonates is inefficient and the yield of peroxydicarbonate produced varies, thus making the polymerization reaction using the peroxydicarbonates initiator(s) vary in reaction time. To make greater volumes, diluents are often used, such as solvents and water. With these diluents there is poor conversion of the reactants resulting in large amounts of undesirable by-products which are formed and which remain in the large reactor to contaminate the polymer that is ultimately produced in the reactor. Solvent dilution results in solvent being present which must be recovered and contaminates the recovery system for recovering unreacted monomer. Also, by making the peroxydicarbonate in the large polymerization vessel, productivity is lowered because the polymerization vessel is occupied with the peroxydicarbonate synthesis process before each batch of polymer can be produced.

Great Britain Patent 1,484,675 proposes to solve these problems by producing the peroxydicarbonates outside of the polymerization vessel in the presence of a solvent to obtain adequate mixing of the reactants. This method is undesirable because the solvent must be removed or else it becomes a contaminant in the polymerization process and contaminates the polymerization process monomer recovery system.

WO 97/27229 patent application proposes to solve the problem by making the peroxydicarbonates outside of the polymerization reactor in a two-step process and adding a water insoluble liquid dialkyl alkanedicarboxylate. The dialkyl alkane dicarboxylate is a plasticizer for the resulting polymer and is undesirable in rigid applications of the polymer. Also, the two-step process is cumbersome and requires excess equipment.

U.S. Pat. No. 4,359,427, Great Britain patent 1,484,675 and WO 97/27229 all teach that the peroxydicarbonates can be produced by reacting a chloroformate with an alkali metal peroxide.

SUMMARY OF THE INVENTION

It has been unexpectedly found that a peroxydicarbonate initiator can be produced at a polymerization site outside of the polymerization vessel which when used in polymerizing ethylenically unsaturated monomers gives high quality polymers. The process for making the peroxydicarbonate of this invention involves first mixing an alkali metal hydroxide with a peroxide to form an alkali metal peroxide. The alkali metal peroxide is added to a mixture of haloformate, dispersant and water to form the desired peroxydicarbonate. The reaction mixture is homogenized during the reaction to give small droplets of peroxydicarbonates. The resulting peroxydicarbonates do not need to be diluted with solvents or plasticizer nor do they need to be purified. The resulting peroxydicarbonates are produced immediately prior to a polymerization reaction and charged to the polymerization vessel and the polymerization reaction is conducted to give a high quality polymer from the ethylenically unsaturated monomer.

DETAILED DESCRIPTION

Peroxydicarbonates produced by this invention have the general formula:

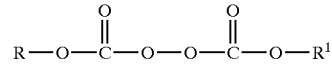

R and $R^1$ are different or identical organic radicals having from 2 to 16 carbon atoms, preferably 2 to 10 carbon atoms, and more preferably from 2 to 6 carbon atoms. The most preferred peroxydicarbonates have R and $R^1$ as identical radicals. Specific examples of R and $R^1$ are alkyl radicals such as ethyl, n-propyl, isopropyl, n-butyl, isobutyl, secondary butyl, amyl, hexyl or 2-ethylhexyl; alkenyl, aryl, alkylaryl, arylalkyl or cycloakyl radicals, or radicals derived from heterocyclic compounds and, particularly radicals such as benzyl, cyclohexyl, cinnamyl, tetrahydrofuryl, and also their substituted derivatives. The most preferred peroxydicarbonates are diethyl peroxydicarbonate, di-n-propyl peroxydicarbonate, di-isopropyl peroxydicarbonate, di-n-butyl peroxydicarbonate, di(secondary butyl) peroxydicarbonate and di(2-ethyl hexyl) peroxydicarbonate.

The haloformates used to produce the peroxydicarbonates have the general formula:

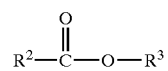

wherein $R^2$ is an organic radical containing from 2 to 16 carbon atoms and $R^3$ is a halogen atom. $R^2$ is the same organic radical as described above for R and $R^1$. $R^3$ is a halogen, such as chlorine, fluorine, iodine or bromine. Preferably $R^3$ is chlorine. One or more than one haloformate may be used to produce the peroxydicarbonate.

At least one dispersant is used in the synthesis of the peroxydicarbonate such as hydrolyzed polyvinyl acetates, alkyl and hydroxyalkyl cellulose ethers such as methyl cellulose, hydroxypropyl methyl cellulose, gelatin, polyvinylpyrrolidone, polyoxyethlyene sorbitan monolaurate, polyacrylic acid, and like compounds. The dispersant is preferably selected to be similar to the dispersant used in the polymerization of the ethylenically unsaturated monomer. For polymerizing vinyl chloride monomer, the preferred dispersant is hydrolyzed polyvinyl acetate having a hydrolysis in the range of about 70% to about 90%. The dispersant is preferably added as a water solution. The level of dispersant used should be sufficient to form a water emulsion of the haloformate. This level is normally from about 0.05 to 0.2 gram of dispersant per gram of haloformate, and is preferably from about 0.075 to about 0.1 gram of dispersant per gram of haloformate. The dispersant is added as a water solution. The solution has from about 1% to about 10% by weight of dispersant in water, preferably from about 3% to about 8% by weight of dispersant in water. Once the reaction to form the peroxydicarbonate is complete, additional dispersant may be added to stabilize the emulsion. Stabilizing the emulsion is particularly important if the peroxydicarbonate is not used shortly after being made.

Water is also used in the synthesis of peroxydicarbonates of this invention. The water is required to disperse the dispersant and other reaction ingredients. Water also assists in removal of the heat resulting from the exothermic reaction. Preferably the water used is demineralized water. The amount of water used is not critical except that the amount necessary to disperse the dispersant and dissolve the alkali metal hydroxide and peroxide must be used. The alkali metal hydroxide and peroxide are used as aqueous solutions and thus provide a portion of the required water. Preferably a minimum amount of water is used to get the required cooling. An excess of water, over that required to disperse the reactants and provide cooling, should be avoided during the reaction so as to give more intimate contact of the reactants. Once the reaction is complete, additional water may be added. Normally the amount of water used for the reaction is from about 5 grams to about 20 grams of water per gram of haloformate, preferably from about 7 grams to about 12 grams of water per gram of haloformate. A majority of the water is added as a result of adding the ingredients as a water solution.

At least one alkali metal peroxide is used in the synthesis of the peroxydicarbonates of this invention. The preferred alkali metal peroxide is sodium peroxide. The alkali peroxide is formed from reacting an inorganic peroxide such as hydrogen peroxide with an alkali metal hydroxide, such as sodium hydroxide, potassium hydroxide, ammonia hydroxide, lithium hydroxide, calcium hydroxide, magnesium hydroxide and alkali metal phosphates. The preferred sodium peroxide is formed by reacting sodium hydroxide with hydrogen peroxide. Two moles of alkali metal hydroxide are used for every one mole of inorganic peroxide. An excess of either reactant can be used, but would not be preferred.

One method to produce the peroxydicarbonates of this invention, is to use two reaction vessels. The reaction vessels may be of any shape and material, but the shape and material of construction should be conducive to being cooled. Metal vessels such as stainless steel pots or pipes are satisfactory. In one vessel, the alkali metal peroxide is produced by mixing the alkali metal hydroxide with inorganic peroxide. The mixture of the alkali metal hydroxide and inorganic peroxide are thoroughly mixed by conventional mechanical agitation to form the alkali metal peroxide. In making the preferred alkali metal peroxide, sodium hydroxide is mixed with hydrogen peroxide to produce sodium peroxide. The preferred sodium hydroxide used is a water solution of sodium hydroxide. The concentration of sodium hydroxide is not critical but the preferred concentration is a 5% to 35 weight % percent solution of sodium hydroxide in water, with the preferred concentration being at 5% to 15 weight % solution of sodium hydroxide. The hydrogen peroxide used is more preferably a 5% to 10 weight % solution of hydrogen peroxide in water.

The mixture used to make the alkali metal peroxide is two moles of alkali metal hydroxide with one mole of inorganic peroxide. The reversible reaction can be shown for the preferred ingredients as:

$$2\ NaOH + H_2O_2 \Leftrightarrow Na_2O_2 + 2\ H_2O$$

The temperature of the reaction needs to be below the decomposition temperature of the alkali metal peroxide. Also, the mixture should be cooled so as not to add heat when later used to make the peroxydicarbonate. For the preferred alkali metal peroxide, the alkali metal peroxide is cooled to less than 28° C. and more preferably to a temperature of from 0° C. to 10° C.

In the second vessel equipped with a homogenizer apparatus and cooling means, the haloformate, dispersant and water are added. The mixture of haloformate, dispersant and water is cooled and homogenized while adding the alkali metal peroxide from the first vessel. It is preferred to start the homogenization before the alkali metal peroxide is added and continue until all of the alkali metal peroxide has been added. The temperature of the mixture of the second vessel should be maintained below the decomposition temperature of the peroxydicarbonate to be formed. For the preferred reactants, the temperature should be maintained below 40° C., preferably below 22° C. and more preferably from 0° C. to 10° C. Because water is present, the mixture should not be cooled low enough to freeze the water, although the freezing temperature of the water in the mixture is lower than 0° C. because of the presence of by-products (salts). If the temperature is above the decomposition temperature of the peroxydicarbonate formed, efficiency is lowered as the peroxydicarbonate will decompose. Decomposition can be observed by foaming caused by the liberation of carbon dioxide when the peroxydicarbonate decomposes. The alkali metal peroxide can be added to the second vessel at a rate which is determined by the ability to cool the second vessel, such as not to exceed the decomposition temperature of the peroxydicarbonate formed. The reaction of the alkali metal peroxide and haloformate are almost instantaneous, but are extremely exothermic. Because of the highly exothermic reaction, it is preferred to meter the alkali metal peroxide from the first vessel to the second vessel containing the haloformate over a period of from about 2 to about 20 minutes. The rate of addition of the alkali metal peroxide is dependant only on the ability to cool the reaction, such as to maintain the reaction temperature below the decomposition temperature of the peroxydicarbonate being formed.

The haloformate, dispersant and water mixture of the second vessel could be added to the first vessel containing the alkali metal peroxide but this method is less efficient in that yields of peroxydicarbonate are lower.

The levels of reactants used in the second vessel are one mole of alkali metal peroxide for every two moles of haloformate. The reaction can be shown for the preferred reactants as:

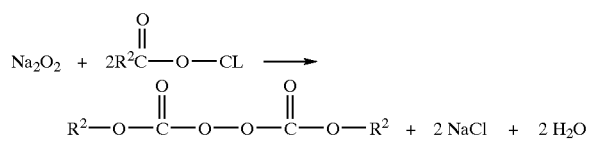

wherein $R^2$ is an ethyl group in the most preferred embodiment of this invention.

Homogenization of the ingredients in the second vessel is very important and a critical feature of this invention as it provides intimate contact between the reactants thus resulting in the need to use less reactants. By using less reactants, the need to dilute the reaction with a solvent or a plasticizer is unnecessary thus resulting in less by-products which are harmful in the polymerization process of the ethylenically unsaturated monomer. The homogenization also gives peroxydicarbonate droplets having a diameter less than 10 microns, preferably less than 5 microns and more preferably from 1 to 4 microns. The small droplet size of peroxydicarbonate is advantageous in producing polymers having low levels of gels.

The type of homogenizer apparatus found to be suitable for larger scale reactions in this invention is an Arde Barinko homogenizer. This type of homogenizer apparatus has a shaft extending into the reactants of the second vessel. The shaft end has narrow slits (teeth) in the fixed stator with a rotating disc having teeth offset from the teeth in the stator, such that the reactants are drawn into and repeatedly cycled through the narrow slits in the stator. For small scale laboratory reactions, a homogenizer of the tissue tearer type such as Fisher Schientic #15-338-51 can be employed.

An alternate method to make the peroxydicarbonates of this invention for use in a polymerization process to produce polymers from ethylenically unsaturated monomers, is to use an in line homogenizer. When using an in-line homogenizer, the haloformate, dispersant and water are injected into a line, such as a pipe. The pipe is connected to a homogenizer. The alkali metal peroxide may be metered into the line just prior to the homogenizer, or preferably in a recirculating line between homogenization passes. This method provides for the homogenization of the haloformate before adding the alkali metal peroxide and homogenization after combining all ingredients. Examples of suitable in-line homogenizers are the those sold under the name Manton Gaulin homogenizer. The ingredients to be homogenized can be passed through the homogenizer multiple times until the desired homogenization is obtained. For making the peroxydicarbonates of this invention, sufficient homogenization should be performed to give a droplet size of the peroxydicarbonate of from about 1 to 10 microns, preferably from about 1 to about 4 microns. The line where the peroxydicarbonates are formed is connected to the polymerization reactor and pumped into the reactor at the desired time. The line is flushed clean with water after the peroxydicarbonate is charged to the polymerization reactor.

If it is desired to produce more than one peroxydicarbonate for use in a polymerization, then the reaction to form the first peroxydicarbonate should be completed before adding the second haloformate and the corresponding alkali metal peroxide. If two different haloformates are mixed and alkali metal peroxide is added, then three different types of peroxydicarbonates will be formed. Two types will be symmetrical with the same end groups on each end, while the third type will have a different end group on each side. Although this type of peroxydicarbonate mixture would function as an initiator for polymerization, it is not the most desirable mixture. The specific amounts of each of the three different types of peroxydicarbonates formed is not believed to be well controlled and can vary from batch to batch. For this reason, it is preferred to complete the reaction of the first peroxydicarbonate before beginning the reaction to form the second peroxydicarbonate. Should a third or subsequent peroxydicarbonate be desired, then the reaction to complete the second peroxydicarbonate should be completed before adding the haloformate to produce the third peroxydicarbonate and so forth for each additional desired peroxydicarbonate.

The reaction in the second vessel to produce the peroxydicarbonate preferably should be completed just prior to when it is needed in the polymerization cycle. Should there be an unplanned delay in using the peroxydicarbonate, the aqueous mixture in the second vessel containing the peroxydicarbonate should be agitated. It is preferred that the second vessel contain an agitation system, as well as the homogenization system. The agitation is necessary because the preferred peroxydicarbonate is heavier than the aqueous salt mixture it is suspended in and will settle to the bottom over time if not agitated. The stability of the other peroxydicarbonates, other than di-ethyl peroxydicarbonate, are greater in that they are less dense, but agitation is still preferred should the use of the peroxydicarbonate be delayed. A simple agitation is preferred rather than continuing to run the homogenizer, since the homogenizer will add heat to the aqueous dispersion of the peroxydicarbonate, which is undesirable. Any type of system for the agitation is acceptable, such as a shaft with blades or a method to bubble inert gas into the vessel, as long as the peroxydicarbonate is not allowed to settle on the bottom of the vessel.

Various peroxydicarbonates can be made by the process of this invention. The nature, or structure of the initiator produced will depend upon the particular haloformate employed in the reaction. The peroxydicarbonates can be used in the suspension polymerization of ethylenically unsaturated monomers. As examples of the ethylenically unsaturated monomers, there may be named the vinyl halides, such as vinyl chloride, vinyl bromide, etc., vinylidene halides, such as vinylidene chloride, and the like, acrylic acid; esters of acrylic acid, such as methyl acrylate, ethyl acrylate, butyl acrylate, octyl acrylate, cyanoethyl acrylate, and the like; methacrylic acid; esters of methacrylic acid such as methyl methacylate, butyl methacrylate, and the like; vinyl acetate; acrylonitrile; syrene and styrene derivatives including alpha-methyl styrene, vinyl toluene, chlorostyrene, vinyl naphthalene; and other monomers having at least one terminal $CH_2=C<$ grouping; mixtures of any one of these types of monomers and other types of ethylenically unsaturated monomers known to those skilled in the art.

The peroxydicarbonates of the present invention are particularly useful in the suspension polymerization of vinyl chloride to make polyvinyl chloride (PVC). The invention is further described in the aqueous suspension polymerization of vinyl chloride.

In the aqueous suspension process to produce PVC from vinyl chloride monomer, the polymerization process is usually conducted at a temperature in the range of about 0° C. to 100° C. However, it is preferred to employ temperatures in the range of about 40° C. to about 70° C., since at these temperatures polymers having the most beneficial properties are produced. The time of the polymerization reaction will vary from about 2 to about 15 hours, preferably from 3 to 6 hours. The aqueous suspension process to produce PVC contains, in addition to the vinyl chloride monomer, water, dispersants, free radical initiator and may optionally contain other ingredients such as buffers, short stop agents, and the like. The aqueous suspension process to produce PVC is a batch process for the reaction and then becomes a continuous process after leaving the reactor. The continuous part of the process involves stripping the residual vinyl chloride monomer from the PVC polymer and recovering the monomer for further use in subsequent polymerizations. Also, the polymer particles are dewatered and dried to a free flowing powder, all as is well understood in the art.

Once the PVC polymerization reaction reaches the desired conversion, which is usually from about 80 to 94 percent conversion of the monomer to polymer, the reaction is stopped and the reactor contents are pumped out to empty the reactor. The empty reactor is then prepared for the next polymerization cycle by flushing with water and coating the walls to prevent build-up of polymer. The flushing and coating cycle consumes about 10 to 20 minutes, which is ample time to conduct the reaction to make the peroxydicarbonate which will be used in the next polymerization cycle.

The peroxydicarbonate made by this invention, together with the by-products of the peroxydicarbonate reaction are charged to the PVC reactor at the desired time to begin the polymerization of the vinyl chloride monomer. The order of charging the ingredients to the PVC reactor is not critical, however it is preferred to charge the peroxydicarbonate after the reactor contents have reached the desired polymerization temperature. If the peroxydicarbonate is added before the desired polymerization temperature is reached, some of it will be used up at the lower temperature and result in less initiator being present for the polymerization. This can be compensated for by adding an excess of peroxydicarbonate, but is less desirable because of increased costs.

The yields of the peroxydicarbonate preparation method of this invention are from about 90 to about 97% yield. A convenient method to determine the yield is to measure the PVC reaction cycle time with a given loading of peroxydicarbonate and compare the reaction time to the theoretical time, as is well understood in the art. The PVC reaction cycle times indicate that the yields of the peroxydicarbonate made by the method of this invention are very reproducible and are at least 90%. A convenient method is to the charge to the PVC reactor with about 10% excess over the theoretical amount required of the peroxydicarbonate produced by this invention. This is to compensate for the less than 100% yield.

The level and selection of a particular type of peroxydicarbonate used in a PVC polymerization reaction will vary depending on the reaction temperature desired and the total reaction cycle time desired. The total cycle time desired is usually determined by the speed at which heat can be removed from the PVC reaction. The speed of heat removal depends on several factors such as the surface area of the reactor available for cooling, the cooling medium temperature, and the coefficient of heat transfer. PVC reactors can be equipped with reflux condensers to enhance the speed of cooling and refrigerated water can be used on the reactor jacket as well as internal cooling surfaces such as baffles.

Normal level of peroxydicarbonate used, when the peroxydicarbonate is di-ethyl peroxydicarbonate is from 0.20 to 1 part by weight per 100 parts by weight of vinyl chloride monomer, preferably from 0.030 to 0.060 part by weight per 100 parts by weight of vinyl chloride monomer. Different peroxydicarbonates require different levels depending on their decomposition rate to form free radicals at a given reaction temperature, and their molecular weight, all is well understood by those skilled in the art. Conventional peroxydicarbonates or other initiators can be used in conjunction with the peroxydicarbonates of this invention to achieve a particular reaction kinetics, although it is not necessary, since multiple peroxydicarbonates can be made in the same vessel by the method of this invention.

One important advantage of this invention is that the entire contents of the vessel where the peroxydicarbonate is produced can be charged to the PVC polymerization reactor. There is no need to purify the peroxydicarbonate nor to dilute it with solvents or plasticizers as is taught by the prior art methods.

The peroxydicarbonates are preferably made on demand, one batch at a time, as needed. This eliminates the need to store the peroxydicarbonate. Of course, the peroxydicarbonates could be made by the method of this invention and stored for later use, but this is less desirable.

The following examples are presented to show the method of making peroxydicarbonate and their subsequent use to produce high quality PVC polymers.

EXAMPLE 1

In this Example di-ethyl peroxydicarbonate is produced by the method of this invention. The preparation of the peroxydicarbonate is carried out in a fume hood. An Arde Barinko homogenizer unit is used. A 15 liter beaker is placed within an acetone-dry ice cooling bath held at approximately −10° C. In addition, an ethylene glycol cooling coil is placed within the beaker. Temperatures of both the reaction mixture and the external cooling bath are monitored continuously via glass thermometers clamped in place. The cooling coil operates at from 4° C. to 10° C. 1200 milliliters of water was placed within the 15 liter steel beaker, followed by 1,000 milliliters of 5 weight percent in water of 72.5% hydrolyzed poly vinyl acetate dispersant and 541 milliliters (596 grams) of ethyl chloroformate. This mixture was homogenized with an Arde Barinko homogenizer for approximately one minute, to facilitate the formation of an emulsion of ethyl chloroformate.

In a separate glass beaker, placed within an ice bath, 4154 milliliters (4391 grams) of a 5 weight percent in water of sodium hydroxide was mixed with 280 milliliters (311 grams) of a 30 weight percent in water of hydrogen peroxide. Mechanical agitation was used in the glass beaker. The mixture was stirred mechanically for approximately 5 minutes, to facilitate the formation of sodium peroxide (which is formed in equilibrium with sodium hydroxide and hydrogen peroxide) as represented by the formula:

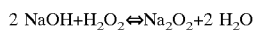

This mixture containing the sodium peroxide was then placed within a glass dropping funnel which was securely clamped above the 15 liter stainless steel beaker containing the ethyl chloroformate. The temperature within the steel beaker was 0° C. The homogenizer was running throughout the synthesis reaction to form the peroxydicarbonate.

The sodium peroxide was added dropwise from the glass dropping funnel, with the addition rate manually adjusted such that the temperature of the reaction mixture did not rise above 10° C. The reaction of the sodium peroxide with the ethyl chloroformate can be represented by the formula:

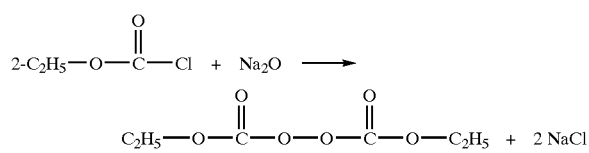

At the end of the addition of the sodium peroxide, which was from 10–15 minutes, the reaction mixture was homogenized for a further 5 minutes while an additional 3500 milliliters of a 5 weight percent in water of 72.5% hydrolyzed poly vinyl acetate was added to stabilize the di-ethyl peroxydicarbonate emulsion.

On a 100% yield basis there would be 489 grams of di-ethyl peroxydicarbonate produced.

The mixture now contains all of the di-ethyl peroxydicarbonate and 72.5% hydrolyzed poly vinyl acetate necessary to provide a dispersed initiator charge for a 4.2 cubic meter size reactor to polymerize vinyl chloride.

If one wishes to produce different peroxydicarbonates, other than di-ethyl peroxydicarbonate, to achieve the same activity on an active oxygen basis, different chloroformates would be required in the procedure described above according to the following table:

TABLE 1

| Peroxydicarbonate made | Chloroformate used | Amount chloroformate used | |
|---|---|---|---|
| | | Grams | Milliliters |
| Di-ethyl peroxydicarbonate | Ethyl chloroformate | 596 | 541 |
| n-propyl peroxydicarbonate | n-propyl chloroformate | 673 | 617 |
| Iso-propyl peroxydicarbonate | Iso-propyl chloroformate | 673 | 624 |
| n-butyl peroxydicarbonate | n-butyl chloroformate | 750 | 698 |
| s-butyl peroxydicarbonate | s-butyl chloroformate | 750 | 714 |
| 2-ethyl hexyl peroxydicarbonate | 2-ethyl hexyl chloroformate | 1058 | 1080 |

The amounts of the other ingredients (other than the chloroformate) and the procedure would be the same as described above for making di-ethyl chloroformate.

EXAMPLE 2

This example is presented to show a vinyl chloride suspension polymerization using the di-ethyl peroxydicarbonate produced in Example 1.

To a clean 4.2 cubic meter polymerization reactor equipped with agitation and cooling was added 1,479.86 kg of vinyl chloride monomer, 2,013.278 kg of hot demineralized water, 3.9173 kg of methyl cellulose dispersant, 2.5243 kg of 88% hydrolyzed poly vinyl acetate dispersant and the aqueous di-ethyl peroxydicarbonate emulsion produced in Example 1. The reaction was started at 56.5° C. and held at this temperature for 45 minutes. At 45 minutes the reaction temperature was reduced by 0.038° C. per minute for 185 minutes to a reaction temperature of 49.5° C. The reaction temperature was held at 49.5° C. until pressure drop occurred. At 312 minutes after the addition of the initiator pressure drop occurred and 591.9 grams of a short-stop agent was added to terminate the reaction. The PVC slurry was stripped of residual monomer and dried. Examination of the internal metal surfaces of the polymerization vessel showed that the vessel was unexpectedly lacking in polymer build-up, which is very advantageous.

This example demonstrates that the di-ethyl peroxydicarbonate produced in Example 1 was very effective in polymerizing vinyl chloride monomer.

EXAMPLE 3

This example is presented to show a standard control vinyl chloride suspension polymerization using a commercially available sec-butyl peroxydicarbonate. The same polymerization vessel (4.2 cubic meters), and reaction ingredients and procedures were followed as in Example 2, except that 669 grams of sec-butyl peroxydicarbonate was used as the initiator. At 291 minutes after the addition of the initiator, pressure drop occurred and the short-stop agent was added. The PVC slurry was stripped of residual monomer and dried. An examination of the internal surfaces indicated that there was some polymer build-up, which is normal for this type of reaction. The polymer build up was greater for this reaction than for the reaction of Example 2, which uses the peroxydicarbonate produced by this invention.

EXAMPLE 4

This example when compared with Examples 5 and 6 is presented to show the superiority of using the di-ethyl peroxydicarbonate produced by this invention over that used in the prior art method of producing the peroxydicarbonate in the PVC reactor vessel. This example is a control for Examples 5 and 6.

A vinyl chloride suspension reaction was conducted in a 55 liter polymerization vessel equipped with agitation and cooling. To a clean 55 liter reactor vessel, the following polymerization ingredients were added:

| | |
|---|---|
| demineralized water | 25.440 Kg |
| Vinyl chloride monomer | 18.544 Kg |
| PVA (72.5%) | 439.898 gr |
| Methyl cellulose | 68.681 gr |
| PVA (88%) | 35.210 gr |
| Sec-butyl peroxydicarbonate | 8.396 gr |

The water was first added and the agitator started. The vinyl chloride monomer (VCM) was added and the reactor contents were heated to 56° C. The dispersants were then added and agitation continued while maintaining the temperature at 56° C. for 10 minutes. At this time the commercially available initiator, secondary-butyl peroxydicarbonate, was added and the reaction started. The reaction temperature was maintained at 56° C. for 49 minutes. The reaction temperature was gradually reduced as in Example 2 for 197 minutes until it reached 50° C. The temperature was maintained at 50° C. until a pressure drop occurred. A pressure drop occurred at 272 minutes after adding the initiator, at which time the reaction was terminated by adding 3.709 gr of a short-stop agent. The PVC resin slurry was stripped of residual monomer and dried.

EXAMPLE 5

This example is presented to show that a vinyl chloride suspension reaction using the di-ethyl peroxydicarbonate produced by the method of this invention is superior to the method used in the prior art of producing the di-ethyl peroxydicarbonate in the polymerization vessel (as is shown in Example 6).

The same 55 liter reactor vessel was used in this example as in Example 4 and the same procedures followed as well as the same reaction ingredients, except that the 8.396 grams of commercially available secondary butyl peroxydicarbonate was replaced with a di-ethyl peroxydicarbonate produced as in Example 1 using 8.56 grams of ethyl chloroformate. Pressure drop occurred at 274 minutes after addition of the initiator and the reaction was terminated at this time by adding a short stop agent as in Example 4. The PVC resin slurry was stripped of residual monomer and dried.

EXAMPLE 6

This example is presented to show the suspension polymerization of vinyl chloride monomer using the prior art method of making di-ethyl peroxydicarbonate in the polymerization vessel, prior to the polymerization.

The same 55 liter reactor was used in this example as in Examples 4 and 5 and the same procedures followed as well as the same reaction ingredients, except that in this example the di-ethyl peroxydicarbonate was produced in the reaction vessel and about a 35% excess of initiator ingredients were used to obtain an equivalent time to pressure drop, because of the inefficiency in making the peroxydicarbonate in the reactor vessel.

To make the initiator in the reactor, 8.1 Kg of water was first charged to the reactor (which is about 32% of the total water used) and the agitator started. It was necessary to have the water level higher than the agitator level in the reactor in order to get agitation for making the initiator. The dispersants (72.5% PVA, 88% PVC and methyl cellulose) were then charged to the reactor and followed by 10.50 grams of ethyl chloroformate, 15.4276 grams of sodium hydroxide, and 5.5628 grams of hydrogen peroxide. The ingredients were mixed for 5 minutes before charging the remaining water. The vinyl chloride monomer was then charged and temperature brought to 56° C. The temperature profile was then the same as in Examples 4 and 5. Pressure drop occurred at 277 minutes and the reaction was stopped as in Examples 4 and 5. The resulting PVC resin slurry was dewatered and dried.

The PVC resins produced in Examples 4, 5 and 6 were tested for properties important to PVC resins and the results are shown in Table III below:

TABLE III

| Resin Property | Example 4 (control) | Example 5 (this invention) | Example 6 (comparative) |
| --- | --- | --- | --- |
| Avg particle size (microns) | 126 | 131 | 146 |
| Particle size distribution | 23 | 23 | 27 |
| % coarse | 0.10 | 0 | 0.10 |
| % fines | 21.48 | 19.40 | 12.61 |
| DOP porosity (ml/gr.) | 0.414 | 0.394 | 0.361 |
| Apparent bulk density (gr/ml.) | 0.419 | 0.424 | 0.452 |
| Funnel flow (seconds) | 28.4 | 27.0 | 22 |
| Yellowness Index | 8.07 | 11.63 | 14.54 |
| DTS - yellow (min) | 14 | 18 | 10 |
| DTS-black (min) | 24 | 29 | 22 |

From the above data it can be seen that the thermal stability and initial color (yellowness index) of the PVC resin made with the initiator produced in the reaction vessel (Example 6) is inferior to the PVC resin produced according to this invention (Example 5). The resin produced by this invention compares much more favorably to the control (Example 4) which uses a conventional commercially available sec-butyl peroxydicarbonate initiator. The yellowness index and the stability (DTS) problems of the prior art method are believed to be caused by the low yield of peroxydicarbonates made in the reactor thus resulting in significant amounts of chloroformate not being converted to peroxydicarbonate due to hydrolysis to ethyl carbonic acid and the resulting detrimental effects on the PVC resin by having these contaminants present in the polymerization.

The above examples and description of the invention is not limited by the specific materials mentioned or examples performed. The invention is intended to be limited only by the claims which follow.

I claim:

1. A process for the polymerization of at least one ethylenically unsaturated monomer comprising
    (a) producing at least one peroxydicarbonate by
        (i) reacting at least one inorganic peroxide with at least one alkali metal hydroxide in a first vessel to form at least one alkali metal peroxide;
        (ii) charging into a second vessel equipped with homogenizing means and cooling means at least one haloformate, at least one dispersant, and water;
        (iii) begin homogenizing the contents of said second vessel; and
        (iv) metering said at least one alkali metal peroxide produced in said first vessel into said second vessel while continuing to homogenize the contents of said second vessel until substantially all of said alkali metal peroxide has reacted with said haloformate to form peroxydicarbonate;
    (b) adding to a polymerization reactor at least one ethylenically unsaturated monomer, water, dispersant, and peroxydicarbonate produced in (a);
    (c) conducting the polymerization reaction to the desired level of conversion of said ethylenically unsaturated monomer to form polymer;
    (d) discharging said polymer from said polymerization reactor;
    (e) stripping said ethylenically unsaturated monomer from said polymer; and
    (f) dewatering and drying said polymer to a free flowing power form, where said first vessel and said second vessel are located exterior of said polymerization reactor.

2. A process of claim 1 wherein the entire contents of said second vessel are charged to said polymerization reactor.

3. A process of claim 1 wherein said peroxydicarbonate has the formula:
    Where R and R1 are different or identical organic radicals containing from 2 to 16 carbon atoms.

4. A process of claim 3 wherein said ethylenically unsaturated monomer is vinyl chloride comonomer.

5. A process of claim 4 wherein said R and $R^1$ of said peroxydicarbonate are identical organic radicals containing from 2 to 8 carbon atoms.

6. A process of claim 5 wherein R and $R^1$ of said peroxydicarbonate are selected from the group consisting of ethyl, n-propyl, and secondary butyl.

7. A process of claim 6 wherein said peroxydicarbonate is di-ethyl peroxydicarbonate.

8. A process of claim 4 wherein said haloformate is a chloroformate.

9. A process of claim 8 said alkali metal hydroxide is sodium hydroxide and said inorganic peroxide is hydrogen peroxide and said dispersant is hydrolyzed polyvinyl acetate having a hydrolysis of about 70% to about 90%.

10. A process of claim 9 the contents of said second vessel are maintained at a temperature below 40° C.

11. A process of claim 10 wherein the contents of said second vessel are maintained at a temperature of from about 0° C. to about 10° C. and wherein said alkali metal peroxide is cooled to a temperature of from about 0° C. to about 10° C. prior to being metered into said second vessel.

12. A process of claim 1 wherein said peroxydicarbonate is substantially free of organic solvents and plasticizing agents for said polymer.

13. A process for the polymerization of at least one ethylenically unsaturated monomer comprising:
   (a) injecting at least one haloformate, at least one dispersant, and water into a line equipped with a cooling means and an in-line homogenizer, wherein said line is connected to a polymerization reactor;
   (b) metering at least one alkali metal peroxide into said line;
   (c) homogenizing the ingredients introduced into said line in steps (a) and (b) to form a peroxydicarbonate,
   (d) injecting said peroxydicarbonate in said line into a polymerization reactor containing said ethylenically unsaturated monomer, dispersant, and water,
   (e) conducting the polymerization to the desired conversion level of monomer to polymer in said polymerization reactor,
   (f) discharging said polymer from said polymerization reactor,
   (g) stripping residual monomer from said polymer and dewatering and drying said polymer to a free flowing powder form.

14. A process of claim 13 wherein said ethylenically unsaturated monomer is vinyl chloride monomer.

15. A process of claim 14 wherein said peroxydicarbonate is selected from the group consisting of di-ethyl peroxydicarbonate, di-n-propyl peroxydicarbonate, di-isopropyl peroxydicarbonate, di-n-butyl peroxydicarbonate and secondary butyl peroxydicarbonate.

16. A process of claim 15 wherein said polymerization is conducted at a temperature of from about 40 ° C. to about 70° C.

17. A process of claim 16 wherein said peroxydicarbonate is di-ethyl peroxydicarbonate, said alkali metal peroxide is sodium peroxide, and said peroxydicarbonate is homogenized sufficient to form droplets of from 1 to 10 microns.

18. A process of claim 1 wherein said dispersant is selected from the group consisting of hydrolyzed polyvinyl acetate, methyl cellulose, hydroxypropyl methyl cellulose, gelatin, polyvinylpyrrolidone, polyoxyethlyene sorbitan monolaurate and polyacrylic acid.

19. A process of claim 18 said dispersant is hydrolyzed polyvinyl acetate having a hydrolysis of from about 70% to about 90%.

20. A process for the polymerization of vinyl chloride monomer comprising:
   (a) producing a peroxydicarbonate by
      (i) reacting hydrogen peroxide with sodium hydroxide in a first vessel to form sodium peroxide;
      (ii) charging into a second vessel equipped with homogenizing means and cooling means at least one chloroformate selected from the group consisting of ethyl chloroformate, n-propyl chloroformate, and sec-butyl chloroformate, water, and a dispersant selected from the group consisting of hydrolyzed polyvinyl acetate, methyl cellulose, hydroxypropyl methyl cellulose, gelatin, polyvinylpyrrolidone, polyoxyethlyene sorbitan monolaurate, and polyacrylic acid;
      (iii) homogenizing the contents of said second vessel; and
      (iv) metering said sodium peroxide produced in said first vessel into said second vessel while continuing to homogenize the contents of said second vessel until substantially all of said sodium peroxide has reacted with said chloroformate to form an peroxydicarbonate;
   (b) adding said vinyl chloride monomer and the contents of said second reactor to a polymerization reactor;
   (c) conducting a polymerization reaction in said polymerization reactor to the desired level of conversion of said vinyl chloride monomer to polyvinyl chloride;
   (d) discharging said polyvinyl chloride from said polymerization reactor;
   (e) stripping said vinyl chloride monomer from said polyvinyl chloride; and
   (f) dewatering and drying said polyvinyl chloride to a free flowing power form, where said first vessel and said second vessel are located exterior of said polymerization reactor.

21. The process of claim 13 wherein the peroxydicarbonate formed in step (c) comprises droplets of a peroxydicarbonate ranging in size from about 1 $\mu$m to about 10 $\mu$m.

* * * * *

UNITED STATES PATENT AND TRADEMARK OFFICE
CERTIFICATE OF CORRECTION

PATENT NO.       : 6,770,719 B2                                       Page 1 of 1
APPLICATION NO.  : 10/132582
DATED            : August 3, 2004
INVENTOR(S)      : Ross James Cozens It is certified that error appears in the above-identified patent and that said Letters Patent is hereby corrected as shown below:

In column 2, lines 54-58 – replace the formula " 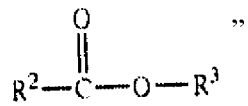 "

with the formula -- 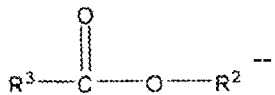 --

In column 5, lines 1-8 – replace the formula

" 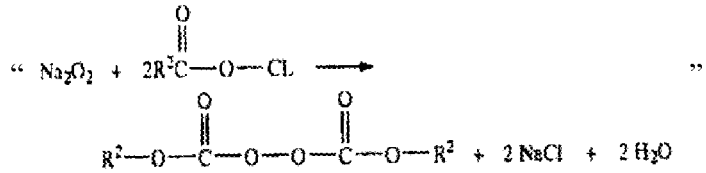 "

with the formula

-- 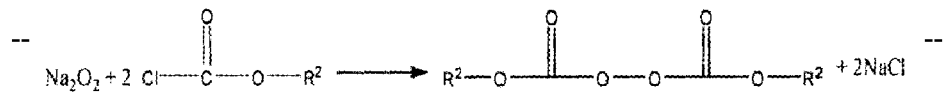 --

Signed and Sealed this

Twentieth Day of January, 2009

JON W. DUDAS
*Director of the United States Patent and Trademark Office*